(12) United States Patent
Ahmed et al.

(10) Patent No.: US 11,801,233 B2
(45) Date of Patent: Oct. 31, 2023

(54) ORAL ELIGLUSTAT TRANSMUCOSAL DELIVERY SYSTEM

(71) Applicant: ABON PHARMACEUTICALS LLC., Northvale, NJ (US)

(72) Inventors: Salah U. Ahmed, New City, NY (US); Yanming Zu, Tenafly, NJ (US); Tahseen A. Chowdhury, Township of Washington, NJ (US); Saad Muntazim, New York, NY (US); Mohammed Irfan Syed, Dumont, NJ (US)

(73) Assignee: ABON PHARMACEUTICALS, LLC, Northvale, NJ (US)

( * ) Notice: Subject to any disclaimer, the term of this patent is extended or adjusted under 35 U.S.C. 154(b) by 0 days.

(21) Appl. No.: 17/811,026

(22) Filed: Jul. 6, 2022

(65) Prior Publication Data

US 2023/0000824 A1    Jan. 5, 2023

Related U.S. Application Data

(63) Continuation of application No. 16/435,071, filed on Jun. 7, 2019, now Pat. No. 11,413,271.
(Continued)

(51) Int. Cl.
*A61K 31/4025*    (2006.01)
*A61K 47/38*    (2006.01)
(Continued)

(52) U.S. Cl.
CPC .......... *A61K 31/4025* (2013.01); *A61K 9/006* (2013.01); *A61K 9/0056* (2013.01);
(Continued)

(58) Field of Classification Search
None
See application file for complete search history.

(56) References Cited

U.S. PATENT DOCUMENTS 6,753,330 B2    6/2004    Takano et al.
2016/0235764 A1    8/2016    Ahmed et al.
(Continued)

FOREIGN PATENT DOCUMENTS

CN    105646442 A    6/2016

OTHER PUBLICATIONS

Wikipedia, "Sorbitol," Nov. 9, 2017, retrieved on Aug. 5, 2019 from https://en.wikipedia.org/w/index.phop?title=Sorbitol&o Id id=809508530.
(Continued)

*Primary Examiner* — Dominic Lazaro
(74) *Attorney, Agent, or Firm* — MEDLER FERRO WOODHOUSE & MILLS PLLC

(57) ABSTRACT

The present disclosure relates to an oral eliglustat transmucosal delivery system. More specifically, the present disclosure is related to an oral transmucosal dosage form comprising a non-disintegrating solid mass comprising (a) a hydrophilic viscosity modifying agent selected from a natural or a synthetic gum with a molecular weight of 10,000 Daltons or greater, (b) a low molecular weight water soluble component with a molecular weight of less than 10,000 Daltons and (c) not more than 70 mg eliglustat, wherein the dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/sec share rate. The dosage forms of as described herein have at least 30% dose reduction as compared to commercially available eliglustat capsules. In addition, unlike the dosing prerequisite for commercially available eliglustat capsules, the oral eliglustat transmucosal dosage form described herein can be administered to patients with Gau-
(Continued)

cher disease type 1 without pre-determination of patients' CYP2D6 genotype.

20 Claims, 2 Drawing Sheets

Related U.S. Application Data

(60) Provisional application No. 62/683,532, filed on Jun. 11, 2018.

(51) Int. Cl.
*A61K 9/00* (2006.01)
*A61K 47/26* (2006.01)
*A61K 47/36* (2006.01)
*A61K 47/32* (2006.01)

(52) U.S. Cl.
CPC .............. *A61K 47/26* (2013.01); *A61K 47/32* (2013.01); *A61K 47/36* (2013.01); *A61K 47/38* (2013.01)

(56) References Cited

U.S. PATENT DOCUMENTS

2017/0129869 A1\* 5/2017 Velaga ............... A61K 31/4025
2018/0015102 A1 1/2018 Ahmed et al.

OTHER PUBLICATIONS

Wikipedia, "Guar," Feb. 27, 2017, retrieved on Aug. 5, 2019 from https://en.wikipedia.org/w/index.php?title=Guard&oldid=767655687.

Written Opinion of tile international Searching Authority in related application PCT/US2019/36137.

\* cited by examiner

A- Carbomer

B- Polycarbophil

C- Xanthan Gum

Viscosity at 10 Shear Rate/Sec

ORAL ELIGLUSTAT TRANSMUCOSAL DELIVERY SYSTEM

FIELD OF THE INVENTION

The present disclosure relates to an oral eliglustat transmucosal delivery system. More specifically, the present disclosure relates to an oral eliglustat transmucosal delivery system. More specifically, the present disclosure is related to an oral transmucosal dosage form comprising a non-disintegrating solid mass comprising (a) a hydrophilic viscosity modifying agent selected from a natural or a synthetic gum with a molecular weight of 10,000 Daltons or greater, (b) a low molecular weight water soluble component with a molecular weight of less than 10,000 Daltons and (c) not more than 70 mg eliglustat, wherein the dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/ sec share rate. The dosage forms as described herein have at least 30% dose reduction as compared to commercially available eliglustat capsules. In addition, unlike the dosing prerequisite for commercially available eliglustat capsules, the oral eliglustat transmucosal dosage form described herein can be administered to patients with Gaucher disease type 1 without pre-determination of patients' CYP2D6 genotype.

BACKGROUND OF THE INVENTION

The effectiveness of a drug depends on the bioavailability of the dosage form delivering the drug. Bioavailability is a measurement of the extent to which a drug reaches the systemic circulation and reflects the fraction of the administered drug that reaches the systemic blood circulation. When a drug in a capsule or tablet is administered orally and swallowed, its bioavailability may be compromised if the drug absorption is limited and the drug further gets metabolized during its absorption from the gastrointestinal tract and transportation via the portal vein to the liver, before reaching the systemic circulation. Absorption mostly depends on the drug's solubility and permeability, as well as the drug stability along the gastrointestinal tract. The drug is usually metabolized in the liver, as a result, only a fraction of the drug reaches the systemic circulation. This is called the first-pass metabolism.

Eliglustat suffers significant the first-pass metabolism when administered orally and swallowed. Commercially available CERDELGA™ (eliglustat) capsules are marketed by Genzyme, a Sanofi Company, as a glucosylceramide synthase inhibitor indicated for the long-term treatment of adult patients with Gaucher disease type 1. Each capsule of CERDELGA™ contains a high dose of eliglustat (84 mg), equivalent to 100 mg of eliglustat tartrate (hemitartrate salt), which is highly water-soluble. CERDELGA™ is extensively metabolized by CYP2D6, an enzyme that is primarily expressed in the liver, therefore experiencing significant first-pass metabolism.

Due to the high first pass effect, the oral bioavailability of CERDELGA™ capsules are extremely low (<5%) especially for the CYP2D6 extensive metabolizers (EMs). Moreover, patients exhibit significantly different pharmacokinetic responses based on each patient's specific CYP2D6 phenotype. For example, in CYP2D6 EMs and intermediate metabolizers (IMs), the eliglustat pharmacokinetics are time-dependent and the systemic exposure increases in a more than dose proportional manner. After multiple oral doses of 84 mg twice daily in EMs, eliglustat systemic exposure ($AUC_{0-12}$) increased up to about 2-fold at steady state compared to after the first dose ($AUC_{0\infty}$). The pharmacokinetics of eliglustat in CYP2D6 poor metabolizers (PMs) is expected to be linear and time independent. Compared to EMs, the systemic exposure following 84 mg twice daily at steady state is 7- to 9-fold higher in PMs. Bioavailability was predicted to be 18.8 and 3.3 times greater for PMs and IMs, respectively, relative to EMs, in whom bioavailability was estimated to be only about 4.17%. (Ref.: CERDELGA™ (eliglustat) capsules package insert; https://www.accessdatalda.gov/drugsatfda_docs/nda/2014/205494Orig1s000ODMemo.pdf).

To achieve therapeutic level of blood concentration in patients with varying metabolism, CYP2D6 phenotype-based dosing regimen has been proposed. Several specific dosing instructions for CERDELGA™ are described in the CERDELGA™ package insert, including: (1) Select patients using an FDA-cleared test for determining CYP2D6 genotype; (2) CYP2D6 EMs or IMs: 84 mg orally twice daily; CYP2D6 PMs: 84 mg orally once daily; (3) Swallow capsules whole, do not crush, dissolve or open capsules; and (4) Avoid eating grapefruit or drinking grapefruit juice (as grapefruit is a strong CYP3A inhibitor). Despite the inconvenience of complying with multiple instructions, significant inter-subject pharmacokinetic variability is observed, as there are numerous levels of the CYP2D6 genotype among patients, covering and spreading over the entire range from PMs to EMs. Due to the high variation in the eliglustat first pass metabolism and the subsequent high variability in the eliglustat blood concentrations, physicians as well as patients face difficulties of identifying the required dose appropriate for the treatment.

Moreover, drugs with high first pass metabolism often require a considerably high oral dose. The current high dose (100 mg of eliglustat tartrate) in CERDELGA™ capsule increases the burden of liver and may lead to hepatotoxicity upon long term usage. In addition, other than the marked individual variation in the drug blood concentrations due to differences in the extent of first pass metabolism, even among the same categories of CYP2D6 poor metabolizers (PMs), intermediate metabolizers (IMs), or extensive metabolizers (EMs), the eliglustat blood concentration or oral bioavailability can also be affected by a co-administered drug competing with eliglustat in the first pass metabolism.

There is no transmucosal dosage form of eliglustat available in market probably due to the overwhelming challenges to fabricate a suitable dosage form. For instance, eliglustat tartrate has a bitter taste. According to US clinical trials, a single-blind, randomized, unbalanced crossover design with five vehicles (with no ingestion) study was performed by Genzyme, a Sanofi Company to assess the palatability of eliglustat prototype liquid formulations in healthy subjects. See, e.g., https://clinicaltrials.gov/ct2/show/NCT02422654?term=Eliglustat&draw=1&rank=8. However, no commercially viable product was developed.

SUMMARY OF THE INVENTION

The present disclosure relates to an oral eliglustat transmucosal delivery system. More specifically, the present disclosure is related to an oral transmucosal dosage form comprising a non-disintegrating solid mass comprising (a) a hydrophilic viscosity modifying agent selected from a natural or a synthetic gum with a molecular weight of 10,000

Daltons or greater, (b) a low molecular weight water soluble component with a molecular weight of less than 10,000 Daltons and (c) not more than 70 mg eliglustat, wherein the dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/sec shear rate. In some embodiments, the eliglustat is about 5 mg to 70 mg as eliglustat. In some embodiments, the eliglustat is 10 mg to 20 mg. In some embodiments, the eliglustat is eliglustat tartrate. In some embodiments, the eliglustat is eliglustat hemitartrate salt.

In some embodiments, at least about 50% (wt/wt) of the non-disintegrating solid mass consists of the hydrophilic viscosity modifying agent and the low molecular weight water soluble component. In some embodiments, the weight ratio of the hydrophilic viscosity modifying agent to the low molecular weight water soluble component is about 5:1 to about 0.1:5.

In some embodiments, the hydrophilic viscosity modifying agent is: (a) a natural gum selected from the group consisting of acacia, tragacanth, xanthan gum, alginates, agar, carrageenan, karaya gum, guar gum, locust bean gum, modified starch, gelatin and combinations thereof; (b) synthetic gum selected from the group consisting of a carbomer, polycarbophil, povidone (polyvinylpyrrolidone), polydextrose, polyethylene oxide (PEO), cellulose derivative, and combinations thereof; or (c) combinations thereof.

In some embodiments, the cellulose derivative is selected from the group consisting of hydroxypropyl methyl cellulose, methylcellulose, hydroxypropyl cellulose, hydroxyethyl cellulose, carboxymethylcellulose sodium, and combinations thereof. In some embodiments, the low molecular weight water soluble component is selected from the group consisting of monosaccharides, disaccharides; and polyols and combinations thereof. In some embodiments, the monosaccharide is selected from the group consisting of glucose, fructose, galactose, and combinations thereof. In some embodiments, the disaccharide is selected from the group consisting of sucrose, lactose, maltose, trehalose and combinations thereof. In some embodiments, the polyol is selected from the group consisting of sorbitol, mannitol, maltitol, erythritol, and hydrogenated starch hydrolysates, xylitol, isomalt, and lactitol, and combinations thereof.

In some embodiments, the dosage form is about 100 mg to about 400 mg. In some embodiments, the dosage form is about 200 mg to about 300 mg. In some embodiments, the oral eliglustat transmucosal system provides an oral cavity residence time of about 5 minutes to about 25 minutes. In some embodiments, the oral eliglustat transmucosal system provides an oral cavity residence time of about 10 minutes to about 20 minutes. In some embodiments, the oral eliglustat transmucosal system provides an oral cavity residence time of about 15 minutes.

In some embodiments, the dosage form provides a microenvironment inside the oral cavity that exhibits a thixotropic behavior with viscosities of at least 50 poises at 1/sec shear rate and at least 10 poises at 10/sec shear rate.

In some embodiments, the dosage form further comprises a taste modifying agent. In some embodiments, the taste modifying agent is neohesperidine dihydrochalcone (NHDC), sucralose, sodium chloride and/or menthol.

In some embodiments, more than 90% of the eliglustat is released within 30 minutes. In some embodiments, more than 50% of eliglustat release is achieved within 20 minutes in the simulated saliva fluid. In some embodiments, the eliglustat achieves systemic circulation faster than an oral dosage form that administers eliglustat primarily to the gastrointestinal tract. In some embodiments, the eliglustat achieves $C_{max}$ within about 30 minutes after administration. In some embodiments, the eliglustat achieves bioavailability at least 30% higher than a conventional oral dosage form administered to the gastrointestinal tract. In some embodiments, the dosage form releases at least about 50% of the eliglustat in 30 minutes when tested using Excella Shaker at 300 rpm in 25 ml simulated saliva fluid (SSF).

In some embodiments, the dosage form is a tablet, a lollipop, or a film. In some embodiments, the dosage form is about 1 mm or greater in thickness, and less than about 30 mm in length.

In some embodiments, disclosure is directed to a method of making an oral transmucosal dosage form comprising (a) mixing (i) a hydrophilic viscosity modifying agent selected from a natural or a synthetic gum with a molecular weight of 10,000 Daltons or greater, (ii) a low molecular weight water soluble component with a molecular weight of less than 10,000 Daltons, and (iii) eliglustat; to form a mixture; and (b) compacting the mixture into a tablet or a lollipop. In some embodiments, the method further comprised moist heating the compacted mixture to form a pliable dosage form. In some embodiments, the dosage form weighs less than about 500 mg.

In some embodiments, the disclosure is directed to a method of making an oral transmucosal dosage form comprising: (a) solubilizing and/or dispersing eliglustat in a hydrophilic viscosity modifying agent selected from a natural or a synthetic gum with a molecular weight of 10,000 Daltons or greater; and (b) casting the mixture into films, wherein the dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/sec shear rate.

In some embodiments, the disclosure is directed to a method of treating a subject with Gaucher disease type 1, the method comprising administering the dosage forms as described herein, wherein the dosage form is administered to the subject without pre-determining the subject's CYP2D6 genotype. In some embodiments, the disclosure is directed to a method of treating a subject with Gaucher disease type 1, the method comprising administering the dosage forms as described herein once daily.

DETAILED DESCRIPTION OF THE INVENTION

Figure 1:
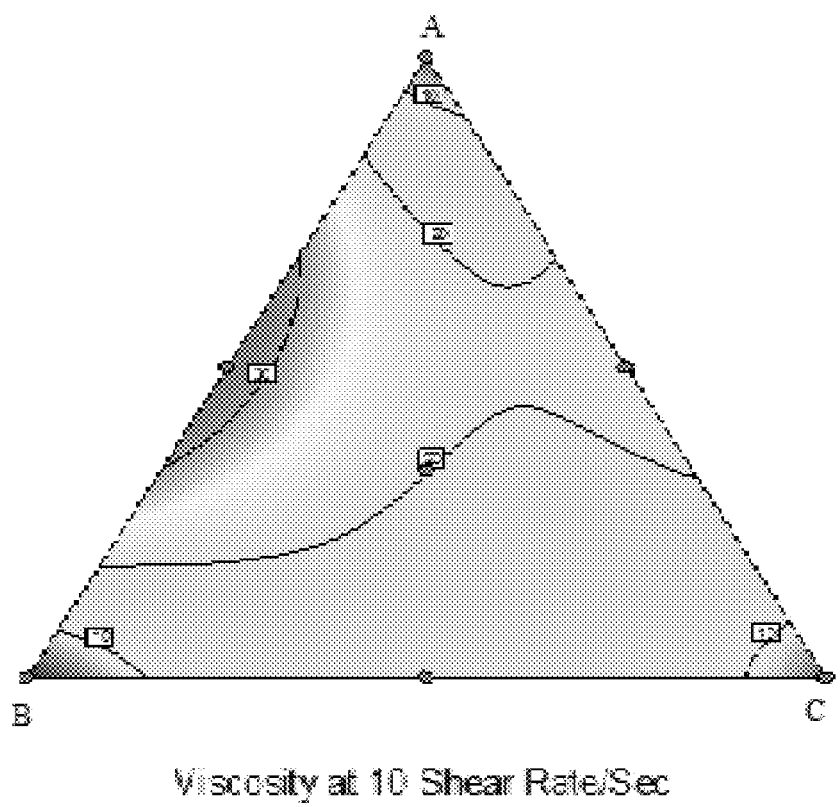
FIG. 1 represents a contour plot generated from viscosity values at 10/sec shear rate using Design-Expert® Software.

The present disclosure relates to an oral eliglustat transmucosal delivery system. In some embodiments, the transmucosal delivery system is a transmucosal dosage form. In some embodiments, the disclosure provides for an improved eliglustat transmucosal dosage form, that can include, but is not limited to, the following characteristics as compared to the commercially available eliglustat oral capsules, CERDELGA™ (Genzyme, Cambridge, Mass.) : (a) at least 30% reduced eliglustat dose, (b) improved bioavailability, (c) reduced metabolism (e.g., CYP2D6 genotype) dependent dose or drug blood concentration variability, (d) improved pharmacological or clinical efficacy, (e) reduced hepatotoxicity upon long term usage, (f) reduced metabolism interference from co-administered drugs, and (g) no dosing prerequisite for the patients' CYP2D6 genotype determination before the dose administration for the Gaucher disease type 1 patients.

In addition, the present disclosure provides for a transmucosal dosage form with the following characteristics, including, but not limited to, (a) suitable eliglustat dosage form size for ease of administration, (b) optimal eliglustat absorption through the oral mucosa in an optimum timely manner,(c) an optimal non-disintegrating retention time of the eliglustat dosage form inside the oral cavity, (d) an optimal viscosity of the microenvironment of the eliglustat dosage form inside the oral cavity, (e) minimal eliglustat drainage down to oropharynx prior to absorption, (f) palatable eliglustat dosage form with minimal or acceptable bitterness inside the oral cavity, and (g) patient acceptance and compliance for the retained eliglustat dosage form inside the oral cavity.

In some embodiments, the eliglustat dose in the oral eliglustat transmucosal dosage form is reduced by at least 30% as compared to the dose in CERDELGA™ (eliglustat) capsules. Improved bioavailability, reduced metabolism dependent variability and hence improved pharmacological or clinical efficacy may be achieved from the oral eliglustat transmucosal dosage form, i.e., delivery system, as described herein, especially compared to CERDELGA™ (eliglustat) capsules. In addition, in some embodiments, the liver enzyme phenotype-based dosing regimen can be avoided with the oral eliglustat transmucosal dosage form described herein. Unlike the dosing prerequisite for CERDELGA™ (eliglustat) capsules, the oral eliglustat transmucosal dosage form described herein can be administered to patients with Gaucher disease type 1 without pre-determination of patients' CYP2D6 genotype.

The development of the oral eliglustat transmucosal delivery system described herein faced several challenges, including, but not limited to obtaining optimal eliglustat absorption, the desired eliglustat blood concentrations, increased patient acceptance and compliance for the retained eliglustat dosage form inside the oral cavity.

The oral eliglustat transmucosal system disclosed herein has the following features, including, but not limited to, (a) the suitable dosage form size of not more than about 500 mg for the ease of administration, (b) the optimal non-disintegrating retention time of dosage form of at least 5 minutes inside the oral cavity to achieve the optimal eliglustat absorption through the oral mucosa in the optimum timely manner, (c) the optimal viscosity of the microenvironment of the eliglustat dosage form inside the oral cavity, exhibiting a thixotropic behavior with viscosities of at least 50 poises at 1/sec shear rate and at least 10 poises at 10/sec shear rate, measured by dispersing a unit dose of eliglustat formulation in deionized water or simulated saliva fluid having a quantity of not more than three times the weight of the eliglustat formulation, and (d) the palatable dosage form with the minimal or acceptable bitterness inside the oral cavity comprising the suitable taste modifying agents.

In some embodiments, the oral transmucosal dosage form comprises a non-disintegrating solid mass, comprising: (a) a hydrophilic viscosity modifying agent selected from a natural or a synthetic gum with a molecular weight of 10,000 Daltons or greater; (b) a low molecular weight water soluble component with a molecular weight of less than 10,000 Daltons, e.g., less than 1,000 Daltons and (c) not more than 70 mg eliglustat, wherein the dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/sec shear rate.

In some embodiments, the eliglustat is about 5 mg to about 70 mg. In some embodiments, the dose of eliglustat is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, or about 70 mg. In some embodiments, the dose of eliglustat is about 10 mg to 20 mg.

In some embodiments, the eliglustat is eliglustat tartrate. In some embodiments, the dose of eliglustat tartrate is about 5 mg, about 10 mg, about 20 mg, about 30 mg, about 40 mg, about 50 mg, about 60 mg, or about 70 mg, which is at least 30% less than the dose in CERDELGA™ (eliglustat) capsules. In some embodiments, the dose of eliglustat is at least 40%, at least 50%, at least 60%, at least 70%, at least 80%, at least 90%, or at least 95% less than the dose in CERDELTA™ (eliglustat) capsules. In some embodiments, the eliglustat is eliglustat hemitartrate salt. In some embodiments, the dose of eliglustat hemitartrate salt is about 10 mg or about 20 mg.

In some embodiments, at least about 50% (wt/wt) of the non-disintegrating solid mass consists of the hydrophilic viscosity modifying agent and the low molecular weight water soluble component. In some embodiments, the weight ratio of the hydrophilic viscosity modifying agent to the low molecular weight water soluble component is about 5:1 to about 0.1:5.

One of the key challenges faced in the development of the oral eliglustat transmucosal delivery system is the microenvironment of the formulation inside the oral cavity for an optimum viscosity. The optimum viscosity can achieve the following characteristics, including, but not limited to, (a) allowing adequate drug release from the dosage form, (b) maximizing the residence of the released drug inside the oral cavity for further absorption, and (c) preventing or minimizing the drug drainage into the stomach. In some embodiments, low viscosity leads to higher potential of the drug drainage beyond buccal cavity to oropharynx, which may result in Pt pass metabolism and reduced drug buccal absorption and bioavailability. Too high viscosity can hinder drug diffusion and absorption via oral mucosa, and therefore decreases drug bioavailability. Moreover, the hydrophilic viscosity modifying agents, usually used by a person skilled in art to control the viscosity of the microenvironment of the formulation inside the oral cavity, generally produce an unpleasant mouthfeel specifically in higher quantities, and hence decrease the patient acceptance and compliance for the retained dosage form inside the oral cavity. Thus, the present disclosure provides an optimum quantity of the hydrophilic viscosity modifying agents to achieve the optimal viscosity of the microenvironment of the eliglustat formulation inside the oral cavity, so that the optimal eliglustat absorption, the desired eliglustat blood concentrations along with the patient acceptance and compliance for the retained eliglustat dosage form inside the oral cavity is achieved.

Saliva, as a naturally occurring oral fluid, is a clear, slightly acidic mucoserous exocrine secretion. The normal pH of saliva is 6 to 7 and can range from 5.3 to 7.8. On average, unstimulated flow rate of saliva is 0.3 mL/min. See, e.g., A review of saliva: normal composition, flow, and function, *The Journal of Prosthetic Dentistry*, Volume 85, No. 2, pages 162-169. Preferably, the oral eliglustat transmucosal dosage form does not disintegrate inside the oral cavity. Normally, the larger the mass of the oral eliglustat transmucosal formulation, the greater the simulated saliva flow rate. The viscosity of the microenvironment of the oral eliglustat transmucosal dosage form inside the oral cavity was evaluated by measuring the viscosity of a unit dose of eliglustat formulation dispersed in deionized water or simulated saliva fluid having a quantity of not more than eight times the weight of the eliglustat formulation. In some embodiments, the viscosity of the microenvironment of the oral eliglustat transmucosal dosage form inside the oral cavity is evaluated by measuring the viscosity of a unit dose of eliglustat formulation dispersed in deionized water or simulated saliva fluid having a quantity of three times the weight of the eliglustat formulation. In some embodiments, the viscosity of the microenvironment of the oral eliglustat transmucosal dosage form inside the oral cavity is evaluated by measuring the viscosity of a unit dose of eliglustat formulation dispersed in deionized water or simulated saliva fluid having a quantity of not more than three times the weight of the eliglustat formulation.

In addition, in some embodiments, components of the oral eliglustat transmucosal delivery system are dispersible inside the oral cavity. In some embodiments, dispersible components can be defined as excipients that are soluble or easily miscible in an aqueous environment or in a biological media such as saliva. The dispersibility of the excipient(s) may enhance the palatability of a dosage form. In some embodiments, 50% of components of oral eliglustat transmucosal delivery system are dispersible inside the oral cavity.

Applicants found that eliglustat reduced the viscosity of some hydrophilic viscosity modifying agents, such as carbomer, polycarbophil, and xanthan gum at various shear rates e.g., Example 1. The data suggest that higher amounts of these hydrophilic viscosity modifying agents need to be incorporated in the eliglustat delivery system to achieve the desired retention time of the formulation, which on the other hand is an undesired attribute as it contributes increased mass and size of the dosage form as well as the unpleasant mouthfeel of these viscosity modifying agents specifically when used at the high amounts thereby hampering the patient acceptance and compliance.

Applicants also observed a synergistic viscosity effect for the combined viscosity modifying agents of carbomer, polycarbophil and/or xanthan gum. See, e.g., Example 2. Moreover, it was further revealed that unlike the viscosity of the single viscosity modifying agent, the viscosity of the combined viscosity modifying agents of carbomer and polycarbophil was increased by eliglustat. In addition, the viscosity of the combined viscosity modifying agents of carbomer, polycarbophil and/or xanthan gum did not change significantly upon addition of eliglustat. See, e.g., Example 3. Thus, an optimized small quantity of the combined viscosity modifying agents of carbomer, polycarbophil and/or xanthan gum can be achieved via various designs of experiment, such as the simplex-centroid design and then the drug release and absorption can be tailored and optimized to achieve the desired blood profile. Applicants also discovered that incorporation of buffering agents, such as disodium hydrogen phosphate increased the viscosity of various single and combined viscosity modifying agents of carbomer, polycarbophil and/or xanthan gum regardless of the presence of eliglustat. See, e.g., Example 4.

In some embodiments, the hydrophilic viscosity modifying agent having a molecular weight of not less than 10,000 Daltons is selected from natural gums such as acacia, tragacanth, xanthan gum, alginates, agar, carrageenan, karaya gum, guar gum, locust bean gum, modified starch and gelatin; and synthetic gums such as carbomer, polycarbophil, calcium polycarbophil, povidone (polyvinylpyrrolidone), polydextrose, polyethylene oxide (PEO) and cellulose derivatives, such as hydroxypropyl methyl cellulose, methylcellulose, hydroxypropyl cellulose, hydroxyethyl cellulose, carboxymethylcellulose sodium, and combinations thereof. Molecular weights of typical hydrophilic viscosity modifying agents are as follows:

| Hydrophilic viscosity modifying agents | MW (Daltons) |
| --- | --- |
| Acacia | 240K-580K |
| Alginates | 20K-240K |
| Carbomer | 700K-4 billion |
| Gelatin | 20K-200K |
| Guar gum | 220K |
| Hydroxypropyl cellulose | 50K to 1.25 million |
| Hydroxypropyl methyl cellulose | 10K to 1.5 Million |
| Locust bean gum | 310K |
| Methyl cellulose | 10K to 220K |
| Modified starch | 50 million-500 million |
| Polyethylene oxide | 100K to 7 million |
| Polycarbophil | 700K-3 to 4 billion |
| Povidone | 2.5K to 3 million |
| Tragacanth | 840K |
| Xanthan gum | 1 Million |

In some embodiments, the low molecular weight water soluble component having a molecular weight of less than 10,000 Daltons is selected from monosaccharides, such as glucose, fructose and galactose; disaccharides such as sucrose, lactose, maltose, and trehalose; and polyols such as sorbitol, mannitol, maltitol, erythritol, and hydrogenated starch hydrolysates, xylitol, isomalt, and lactitol, and combinations thereof. Molecular weights of typical water soluble components are as follows:

| Water soluble components | MW (Daltons) |
| --- | --- |
| Erythritol | 122.12 |
| Fructose | 180.16 |
| Galactose | 342.3 |
| Glucose | 180 |
| Isomalt | 344-380 |
| Lactitol | 344-380 |
| Lactose anhydrous | 342.3 |
| Lactose monohydrate | 360.31 |
| Maltitol | 344.32 |
| Maltose | 342.3-360.31 |
| Mannitol | 182.17 |
| Sorbitol | 182.17 |
| Sucrose | 342.3 |
| Trehalose (anhyd, dihydrate) | 342-378 |
| Xylitol | 152.15 |

Preferably, for the ease of administration, the weight of the oral eliglustat transmucosal delivery system is not more than about 500 mg. Thus, in some embodiments, the oral eliglustat transmucosal dosage form is less than about 500 mg. In some embodiments, the dosage form is about 100 mg to about 400 mg. In some embodiments, the dosage form is about 200 mg to about 300 mg. In some embodiments, the weight of the oral eliglustat transmucosal delivery system is about 100 mg, about 200 mg, about 300 mg or about 400 mg.

Another one of the primary challenges is the retention of the formulation inside the oral cavity for an optimum period of time. Typically, the longer the retention time of the formulation inside the oral cavity, the better the drug absorption. However, too long retention time leads to increased saliva production and therefore greater propensity of swallowing the drug with the saliva, which may lead to $1^{st}$ pass metabolism and reduced drug buccal absorption and bioavailability. Meanwhile, the inherent bitterness of eliglustat reduces the patient acceptance and compliance for the retained dosage form inside the oral cavity, especially when the retention time is too long. In some embodiments, in order to achieve an optimal absorption, the oral cavity residence time of the eliglustat dosage form is at least 5 minutes. Thus, in some embodiments, the oral eliglustat transmucosal dosage form provides an oral cavity residence time of at least about 5 minutes. In some embodiments, the oral cavity residence time is about 5 minutes to about 25 minutes. In some embodiments, the oral cavity residence time is about 10 minutes to about 20 minutes. In some embodiments, the oral cavity residence time is about 15 minutes.

In some embodiments, the oral eliglustat transmucosal dosage form generates a microenvironment inside the oral cavity exhibiting a thixotropic behavior with viscosities of at least 50 poises at 1/sec shear rate and at least 10 poises at 10/sec shear rate, measured by dispersing a unit dose of eliglustat formulation in deionized water or simulated saliva fluid having a quantity of not more than three times the weight of the eliglustat formulation. In some embodiments, the oral eliglustat transmucosal dosage form forms a microenvironment inside the oral cavity exhibiting a thixotropic behavior with viscosities of at least 100 poises at 1/sec shear rate and at least 20 poises at 10/sec shear rate.

In some embodiments, the oral eliglustat transmucosal dosage form further comprises a taste modifying agent. In some embodiments, the taste modifying agent is selected from lecithin, saccharin sodium, acesulfame potassium, aspartame, maltodextrin, neotame, neohesperidine dihydrochalcone (NHDC), sucralose, sodium chloride, zinc sulfate, citric acid, tartaric acid, lemon, menthol, peppermint, and combinations thereof.

It was found that mixtures of the taste modifying agents of neohesperidine dihydrochalcone (NHDC), sucralose, sodium chloride and/or menthol, and the viscosity modifying agents of carbomer, polycarbophil and/or xanthan gum made the oral eliglustat transmucosal system palatable (Example 5). Furthermore, the resulting oral eliglustat transmucosal system provided a desired oral cavity residence time of about 15 minutes (5 to 25 minutes). An in-vitro residence time evaluation method was also developed. The data were comparable to the human evaluation results.

In some embodiments, the oral eliglustat transmucosal dosage form further comprises a buffering agent. In some embodiments, the buffering agent is selected from mineral buffers, such as phosphate, tris, and citrate, and organic buffers such as glycine, and combinations thereof.

In some embodiments, more than 90% of the eliglustat is released within 30 minutes and more than 50% of eliglustat release is achieved within 20 minutes in simulated saliva fluid.

In some embodiments, the oral eliglustat transmucosal dosage form achieves systemic circulation faster than an oral dosage form that administers eliglustat primarily to a gastrointestinal tract. For example, in some embodiments, the oral eliglustat transmucosal dosage form achieves systemic circulation 10%-90% faster, 20% to 80% faster, 30% to 70% faster or 40% to 60% faster than an oral dosage form that administers eliglustat primarily to a gastrointestinal tract. In some embodiments, the oral eliglustat transmucosal dosage form achieves $C_{max}$ within about 30 minutes after administration. In some embodiments, the oral eliglustat transmucosal dosage form achieves bioavailability at least 30% higher than a conventional oral dosage form administered to a gastrointestinal tract. In some embodiments, the oral eliglustat transmucosal dosage form releases at least about 50% of the eliglustat in 30 minutes when tested using Excella Shaker at 300 rpm in 25 ml simulated saliva fluid (SSF).

In some embodiments, the oral eliglustat transmucosal delivery system is a tablet.

In some embodiments, the oral eliglustat transmucosal delivery system is a lollipop.

In some embodiments, the oral eliglustat transmucosal delivery system is a film.

In some embodiments, the oral eliglustat transmucosal dosage form has a physical shape suitable to be placed in the oral cavity having a thickness of not less than 1 mm and the longest dimension of not more than 30 mm.

In some embodiments, the oral eliglustat transmucosal dosage form has either a round, oval, rectangular, triangular, or cylinder shape having a thickness of not less than 1 mm and the longest dimension of not more than 30 mm.

In some embodiments, the method of making the oral eliglustat transmucosal delivery system comprises the steps of i) mixing excipients comprising at least one hydrophilic viscosity modifying agent with eliglustat, ii) compressing the mixture into tablets or lollipops, and iii) optionally moist heating the compact mass to form a pliable dosage form.

In some embodiments, the hydrophilic viscosity modifying agent is a natural of a synthetic gum having a molecular weight of 10,000 Daltons or greater. In some embodiments, step (i) further comprises mixing the hydrophilic viscosity modifying agent and the eliglustat with a low molecular weight water soluble component with a molecular weight of less than 10,000 Daltons. In some embodiments, the oral eliglustat transmucosal dosage form formed by the method weighs less than about 500 mg.

In some embodiments, the method of making an oral eliglustat transmucosal dosage form comprises the steps of i) solubilizing and/or dispersing eliglustat in excipients comprising at least one hydrophilic viscosity modifying agent selected from natural and synthetic gums having a molecular weight of not less than 10,000 Daltons, and ii) casting the mixture into films. In some embodiments, the oral eliglustat transmucosal dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/sec shear rate.

In some embodiments, the oral eliglustat transmucosal dosage form can be administered to patients with Gaucher disease type 1 without pre-determination of patients' CYP2D6 genotype.

In some embodiments, the oral eliglustat transmucosal dosage form can be administered to patients with Gaucher disease type 1 once a day, preferably once a day.

EXAMPLES

Example 1

Surprisingly, it was found that eliglustat (as hemitartrate salt) reduced the viscosity of carbomer, polycarbophil, and xanthan gum at various shear rates. As depicted in Table 1, the hydrophilic viscosity modifying agents presented thixotropic viscosity behaviors upon shearing in deionized water. However, viscosities of all the viscosity modifying agents were significantly decreased upon the addition of eliglustat at a weight ratio of 10:1 (viscosity modifying agent: eliglustat) at all the shear rates. For example, for the 1% carbomer in deionized water, the viscosity was 12.92 poise at 10/sec shear rate, however, its viscosity dropped to 3.60 poise at the same shear rate upon the addition of 0.1% eliglustat. Furthermore, for the 1% polycarbophil in deionized water, the viscosity was 17.6 poise at 1/sec shear rate, nevertheless, its viscosity dropped to about 1 poise at the same shear rate after the addition of 0.1% eliglustat. The data indicate that eliglustat decreases the viscosity of carbomer, polycarbophil, and xanthan gum at all the shear rates.

TABLE 1

| Composition in deionized water | Viscosity (poise) at various/sec shear rates | | |
|---|---|---|---|
| (% w/v) | 1 | 10 | 100 |
| 1% Carbomer | 75.79 | 12.92 | 2.99 |
| 1% Carbomer + 0.1% Eliglustat | 16.95 | 3.60 | 1.05 |
| 1% Polycarbophil | 17.60 | 3.86 | 1.10 |
| 1% Polycarbophil + 0.1% Eliglustat | 1.04 | 0.57 | 0.30 |
| 1% Xanthan gum | 46.10 | 6.98 | 1.31 |
| 1% Xanthan gum + 0.1% Eliglustat | 18.83 | 3.94 | 1.14 |

Example 2

Unexpectedly, a synergistic viscosity effect was discovered for the combined viscosity modifying agents of carbomer, polycarbophil and/or xanthan gum. Based on the system composition and the individual arithmetic contribution from each viscosity modifying agent, a theoretical viscosity was calculated using the equation, $$\text{Viscosity} = V_a \times F_a + V_b \times F_b + V_c \times F_c \quad (Eq.1)$$

where "$V_a$, $V_b$ or $V_c$" is viscosity of each single viscosity modifying agent, and "$F_a$, $F_b$ or $F_c$" is weight fraction of each single viscosity modifying agent in the combined viscosity modifying agents.

However, as illustrated in Table 2, the actual measured viscosity was significantly higher than the calculated arithmetic values based on each individual's proportional contribution. For instance, for the 1% combination of carbomer and polycarbophil (0.5:0.5 w:w) in deionized water, the theoretical calculated viscosity is 9.08 poise at 10/sec shear rate, however, the actual measured viscosity was 11.92 poise at the same shear rate, which is about 30% higher than the calculation value. For the 1% combination of polycarbophil and xanthan gum (0.5:0.5 w:w) in deionized water, the theoretical calculated viscosity is 6.11 poise at 10/sec shear rate, nevertheless, the actual measured viscosity was 22.63 poise at the same shear rate, which is about 270% higher than the calculation value. In addition, for the 1% combination of carbomer, polycarbophil and xanthan gum (0.33:0.33:0.33 w:w:w) in deionized water, the theoretical calculated viscosity is 8.38 poise at 10/sec shear rate, yet, the actual measured viscosity was 22.87 poise at the same shear rate, which is about 170% greater than the calculation value. The data show that the combined viscosity modifying agents of carbomer, polycarbophil and/or xanthan gum provide synergistic viscosity effects.

TABLE 2

| | Viscosity (poise) at 10/sec shear rate | |
|---|---|---|
| Composition in deionized water (% w/v) | Actual | Calculated |
| 1% Carbomer | 12.92 | — |
| 1% Polycarbophil | 5.23 | — |
| 1% Xanthan gum | 6.98 | — |
| 1% Carbomer:Polycarbophil (0.5:0.5 w:w) | 11.92 | 9.08 |
| 1% Carbomer:Xanthan gum (0.5:0.5 w:w) | 19.30 | 9.95 |
| 1% Polycarbophil:Xanthan gum (0.5:0.5 w:w) | 22.63 | 6.11 |
| 1% Carbomer:Polycarbophil:Xanthan gum (0.33:0.33:0.33 w:w:w) | 22.87 | 8.38 |

Example 3

Surprisingly, it was further revealed that unlike the viscosity of the single viscosity modifying agent, the viscosity of the combination of viscosity modifying agents of carbomer and polycarbophil was increased by eliglustat. As shown in Table 3, for the 1% carbomer: polycarbophil (0.5:0.5 w:w) in deionized water, the viscosity was 11.92 poise at 10/sec shear rate, and its viscosity increased 33.8 poise at the same shear rate upon the addition of 0.1% eliglustat. Moreover, the viscosity of the combined viscosity modifying agents of carbomer, polycarbophil and/or xanthan gum did not change significantly upon addition of eliglustat. For example, for the 1% carbomer: polycarbophil: xanthan gum (0.33:0.33:0.33 w:w:w) in deionized water, the viscosity was 22.87 poise at 10/sec shear rate, and the incorporation of 0.1% eliglustat did not change significantly its viscosity at the same shear rate (20.05 poise).

TABLE 3

| Composition in deionized water (% w/v) | Viscosity (poise) at 10/sec shear rate |
|---|---|
| 1% Carbomer:Polycarbophil (0.5:0.5 w:w) | 11.92 |
| 1% Carbomer:Polycarbophil (0.5:0.5 w:w) + 0.1% Eliglustat | 33.8 |
| 1% Carbomer:Xanthan gum (0.5:0.5 w:w) | 19.3 |
| 1% Carbomer:Xanthan gum (0.5:0.5 w:w) + 0.1% Eliglustat | 22.34 |
| 1% Polycarbophil:Xanthan gum (0.5:0.5 w:w) | 22.63 |
| 1% Polycarbophil:Xanthan gum (0.5:0.5 w:w) + 0.1% Eliglustat | 19.65 |
| 1% Carbomer:Polycarbophil:Xanthan gum (0.33:0.33:0.33 w:w:w) | 22.87 |
| 1% Carbomer:Polycarbophil:Xanthan gum (0.33:0.33:0.33 w:w:w) + 0.1% Eliglustat | 20.05 |

Moreover, a simplex-centroid design was carried out to evaluate the impact of various combination viscosity modifying agents on viscosity at the presence of eliglustat. The experimental design and results are reported in Table 4. The polynomial equation for viscosity generated from the viscosity values at 10/sec shear rate using the simplex-centroid design for the combined viscosity modifying agents of carbomer, polycarbophil and/or xanthan gum at the presence of eliglustat is:

$$\text{Viscosity} = 3.6a + 0.7b + 3.9c + 126.7ab + 74.3ac + 69.3bc - 343.7abc \quad (Eq.2)$$

where "a, b and c" refers to proportions of carbomer, polycarbophil and xanthan gum respectively in the system. A contour plot generated from viscosity values at 10/sec shear rate using Design-Expert® Software is depicted in FIG. 1. In this figure, apex A corresponds to carbomer, apex B corresponds to polycarbophil and apex C corresponds to xanthan gum.

TABLE 4

| Composition in deionized water (% w/v) | Viscosity (poise) at 10/sec shear rate |
|---|---|
| 1% Carbomer + 0.1% Eliglustat | 3.60 |
| 1% Polycarbophil + 0.1% Eliglustat | 0.72 |
| 1% Xanthan gum + 0.1% Eliglustat | 3.94 |
| 1% Carbomer:Polycarbophil (0.5:0.5 w:w) + 0.1% Eliglustat | 33.83 |
| 1% Carbomer:Xanthan gum (0.5:0.5 w:w) + 0.1% Eliglustat | 22.34 |

TABLE 4-continued

| Composition in deionized water (% w/v) | Viscosity (poise) at 10/sec shear rate |
|---|---|
| 1% Polycarbophil:Xanthan gum (0.5:0.5 w:w) + 0.1% Eliglustat | 19.65 |
| 1% Carbomer:Polycarbophil:Xanthan gum (0.33:0.33:0.33 w:w:w) + 0.1% Eliglustat | 20.05 |

Example 4

It was also revealed that incorporation of buffering agents, such as disodium hydrogen phosphate increased the viscosity of various single and combined viscosity modifying agents of carbomer, polycarbophil and/or xanthan gum, regardless of the presence of eliglustat. Various oral eliglustat transmucosal systems comprising various single and combined viscosity modifying agents of carbomer, polycarbophil and/or xanthan gum, with or without disodium hydrogen phosphate, were made by direct blending process. The formulation compositions are listed in Table 5. Each unit composition contains 50 mg hydroxypropylmethyl cellulose (HPMC) K4M, as its viscosity is negligible compared to any single or combined viscosity modifying agents of carbomer, polycarbophil and/or xanthan gum when used at the same level. The viscosity of each dose unit in deionized water having a quantity (2 mL) of eight times the weight of the eliglustat formulation was measured. The viscosity data is presented in Table 6. The dose unit of eliglustat without any single or combined viscosity modifying agents of carbomer, polycarbophil and/or xanthan gum had a viscosity of about 24 poise at 10/sec shear rate.

TABLE 5

| | mg/dose | | | | | | |
|---|---|---|---|---|---|---|---|
| Ingredients | X03A | X04A | X05A | X06A | X07A | X08A | X09A |
| Mannitol | 78 | 78 | 78 | 78 | 78 | 78 | 78 |
| Sorbitol | 96.5 | 96.5 | 96.5 | 96.5 | 96.5 | 96.5 | 96.5 |
| HPMC K4M | 50 | 50 | 50 | 50 | 50 | 50 | 50 |
| Carbomer | 3 | 2 | 3 | 0 | 6 | 0 | 0 |
| Polycarbophil | 3 | 2 | 0 | 3 | 0 | 6 | 0 |
| Xanthan Gum | 0 | 2 | 3 | 3 | 0 | 0 | 6 |
| Sucralose | 0.5 | 0.5 | 0.5 | 0.5 | 0.5 | 0.5 | 0.5 |
| PHA Peppermint | 0.5 | 0.5 | 0.5 | 0.5 | 0.5 | 0.5 | 0.5 |
| Menthol | 0.5 | 0.5 | 0.5 | 0.5 | 0.5 | 0.5 | 0.5 |
| Neohesperidine Dihydrochalcone (NHDC) | 0.075 | 0.075 | 0.075 | 0.075 | 0.075 | 0.075 | 0.075 |
| Talc | 3 | 3 | 3 | 3 | 3 | 3 | 3 |
| Magnesium Stearate | 0.925 | 0.925 | 0.925 | 0.925 | 0.925 | 0.925 | 0.925 |
| Eliglustat tartrate (equivalent to 8.4 mg of eliglustat) | 10 | 10 | 10 | 10 | 10 | 10 | 10 |
| Total w/o Na$_2$HPO$_4$ | 246 | 246 | 246 | 246 | 246 | 246 | 246 |
| Disodium Hydrogen Phosphate | 4 | 4 | 4 | 4 | 4 | 4 | 4 |
| Total w/Na$_2$HPO$_4$ | 250 | 250 | 250 | 250 | 250 | 250 | 250 |

As shown in Table 6, for the eliglustat dose unit comprising the combined viscosity modifying agents of 2 mg carbomer, 2 mg polycarbophil and 2 mg xanthan gum without disodium hydrogen phosphate in 2 mL deionized water, the viscosity was 50.0 poise at 10/sec shear rate, and its viscosity tripled to 168.8 poise at the same shear rate upon the incorporation of the buffering agent, disodium hydrogen phosphate. For the eliglustat dose unit comprising a single viscosity modifying agent of 6 mg carbomer, without disodium hydrogen phosphate, the viscosity was 74.3 poise at 10/sec shear rate, and its viscosity more than doubled to 154.5 poise at the same shear rate after the addition of disodium hydrogen phosphate. There was only one exception. The addition of disodium hydrogen phosphate didn't increase the system viscosity for the eliglustat dose unit comprising a single viscosity modifying agent of 6 mg xanthan gum.

TABLE 6

| | | X03A | X04A | X05A | X06A | X07A | X08A | X09A |
|---|---|---|---|---|---|---|---|---|
| Carbomer | | 3 mg | 2 mg | 3 mg | 0 mg | 6 mg | 0 mg | 0 mg |
| Polycarbophil | | 3 mg | 2 mg | 0 mg | 3 mg | 0 mg | 6 mg | 0 mg |
| Xanthan Gum | | 0 mg | 2 mg | 3 mg | 3 mg | 0 mg | 0 mg | 6 mg |
| Blend w/o | 1/sec | 114.6 | 99.8 | 172.4 | 145.6 | 114.6 | 125.1 | 349.1 |

TABLE 6-continued

|  |  | X03A | X04A | X05A | X06A | X07A | X08A | X09A |
|---|---|---|---|---|---|---|---|---|
| Na$_2$HPO$_4$ | 10/sec | 71.1 | 50.0 | 73.1 | 61.9 | 74.3 | 77.2 | 139.1 |
| (246 mg) Viscosity (poise) | 100/sec | 29.0 | 22.1 | 28.6 | 24.6 | 33.0 | 34.4 | 44.7 |
| Blend w/ | 1/sec | 202.2 | 387.3 | 298.0 | 315.9 | 289.6 | 155.7 | 217.5 |
| Na$_2$HPO$_4$ | 10/sec | 113.7 | 168.8 | 126.3 | 141.9 | 154.5 | 96.0 | 87.4 |
| (250 mg) Viscosity (poise) | 100/sec | 37.7 | 52.3 | 43.3 | 49.6 | 52.0 | 40.0 | 29.6 |

Example 5

It was also found that mixtures of the taste modifying agents of neohesperidine dihydrochalcone (NHDC), sucralose, sodium chloride and/or menthol, and the viscosity modifying agents of carbomer, polycarbophil and/or xanthan gum made the oral eliglustat transmucosal system palatable. The composition of formulation X04A comprising the combined viscosity modifying agents of 2 mg carbomer, 2 mg polycarbophil and 2 mg xanthan gum and disodium hydrogen phosphate as shown in Table 5 was further compressed into tablets. The tablets have a round shape having a thickness of about 4 mm and a diameter of about 10 mm. The palatability of the active tablet (X04A) was evaluated in human volunteers. A bitterness scale of 1 to 5 was set. The bitterness level of the eliglustat formulation without any taste modifying agents such as neohesperidine dihydrochalcone (NHDC), sucralose, sodium chloride or menthol, was identified as 5 or being the worst. A bittiness level of equal to or less than 3 was deemed palatable. The bitterness level of the active tablet (X04A) was found to be 3 and considered palatable (Table 7).

TABLE 7

| Organoleptic evaluation | Formulation X04A | Bitterness Level | Palatability |
|---|---|---|---|
| In-vivo Test | Active Tablet | 3 | Palatable |

Meanwhile, a placebo with the X04A composition was also compressed into tablets. The oral residence time of the placebo tablet was evaluated in human volunteers. The residence time of both the placebo and active tablets was measured using a 125 mL conical flask on an Excella Shaker with 75 grams 8 mm beads in 25 mL deionized water at 350 rpm and simulated saliva fluid (SSF, pH 6.75) at 300 rpm. The simulated saliva fluid composition and preparation technique was taken from Wong et al. (Peh KK, Wong CF. Polymeric films as vehicles for buccal delivery: Swelling, Mechanical and Bioadhesive properties. *J Pharm Pharm Sci* 1999; 2:53-61). The residence time results are presented in Table 8. The resulting oral eliglustat transmucosal system (X04A) provided a desired oral cavity residence time of about 15 minutes (5 to 25 minutes). An in-vitro residence time evaluation method was also developed. The data were comparable to the human evaluation results (Table 8).

TABLE 8

| Residence Time | Media | Deionized Water | SSF (pH 6.75) |
|---|---|---|---|
| In-vitro Test | Placebo Tablet | 12 minutes | 10 minutes |
|  | Active Tablet | 12 minutes | 10 minutes |
| In-vivo Test | Placebo Tablet | 18 minutes | |

Figure 2:
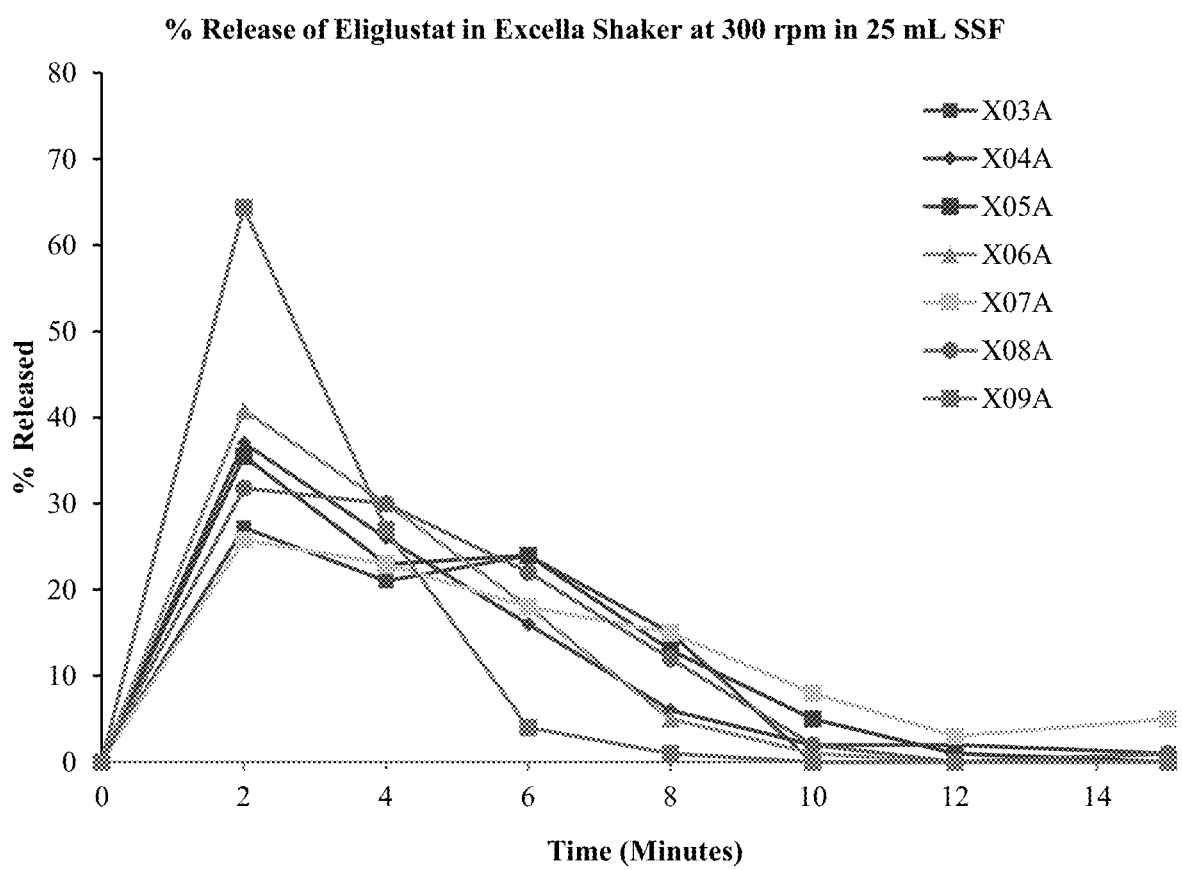
FIG. 2 represents the release profiles of eliglustat dosage forms of the formulations of Table 5, evaluated using a 125 mL conical flask on an Excella Shaker with 75 grams 8 mm beads in 25 mL simulated saliva fluid (SSF, pH 6.75) at 300 rpm.

In addition, various compositions of the oral eliglustat transmucosal systems, containing disodium hydrogen phosphate as shown in Table 5, were compressed into tablets. The dissolution of these tablets was evaluated using a 125 mL conical flask on an Excella Shaker with 75 grams 8 mm beads in 25 mL simulated saliva fluid (SSF, pH 6.75) at 300 rpm. The percent eliglustat release profiles are displayed in FIG. 2. These tablets exhibited immediate release characteristics and the maximum percent release was achieved within 10 minutes for all the formulation compositions.

Oral eliglustat transmucosal formulations with various combinations of the taste modifying agents of neohesperidine dihydrochalcone (NHDC), sucralose, sodium chloride and/or menthol, and the viscosity modifying agents of carbomer, polycarbophil and/or xanthan gum were also made for the bitterness and palatability evaluation. The formulation compositions are given in Table 9. Excipients were mixed with eliglustat, and the mixture was compressed into tablets. Similarly, these tablets have a round shape having a thickness of about 4 mm and a diameter of about 10 mm. One unit dose of these eliglustat formulae were dispersed in deionized water having a quantity of three times the weight of the eliglustat formulation and the viscosity was measured at various shear rates. The viscosity data is presented in Table 10. The bitterness and palatability of these oral eliglustat transmucosal formulations were evaluated in human volunteers and are presented in Table 11. It was revealed that by incorporating sodium chloride into the formulation composition of X04A, the bitterness level of the tablet (X21A) was reduced from 3 to 2. All the oral eliglustat transmucosal formulations with various combinations of the taste modifying agents of neohesperidine dihydrochalcone (NHDC), sucralose, sodium chloride and/or menthol, and the viscosity modifying agents of carbomer, polycarbophil and/or xanthan gum were found to be palatable with bitterness levels of not more than 2.

TABLE 9

| | mg/dose | | | |
|---|---|---|---|---|
| Components | X17A | X18A | X20A | X21A |
| Eliglustat tartrate (equivalent to 8.4 mg of eliglustat) | 10 | 10 | 10 | 10 |
| Mannitol | 122 | 112 | 78 | 78 |
| Sorbitol | 100 | 100 | 96.5 | 96.5 |
| HPMC K4M | 50 | 50 | 50 | 50 |
| Carbomer | 2 | 2 | 2 | 2 |
| Polycarbophil | 2 | 2 | 2 | 2 |
| Xanthan Gum | 2 | 2 | 2 | 2 |
| Disodium Hydrogen Phosphate | — | — | 4 | 4 |
| Sucralose | 2 | 2 | 0.5 | 0.5 |
| PHA Peppermint | 2 | 2 | 0.5 | 0.5 |
| Sodium Chloride | — | 10 | — | 10 |
| Menthol | 1 | 1 | 0.5 | 0.5 |

TABLE 9-continued

| Components | mg/dose | | | |
|---|---|---|---|---|
| | X17A | X18A | X20A | X21A |
| Neohesperidine Dihydrochalcone (NHDC) | 3 | 3 | 0.075 | 0.075 |
| Neotame | — | — | 1.00 | — |
| Talc | 3 | 3 | 3 | 3 |
| Magnesium Stearate | 1 | 1 | 0.925 | 0.925 |
| Total | 300 | 300 | 251 | 260 |

TABLE 10

| Shear rates (/sec) | X17A | X18A | X20A | X21A |
|---|---|---|---|---|
| | Viscosity (Poise) | | | |
| 1 | 3692 | 5117 | 4934 | 5754 |
| 10 | 970.3 | 1281 | 1185 | 1072 |
| 100 | 151.2 | 192.9 | 142.8 | 134.8 |

TABLE 11

| Organoleptic evaluation | X17A | X18A | X20A | X21A |
|---|---|---|---|---|
| Bitterness Level | 2 | 1 | 2 | 2 |
| Palatability | Palatable | Palatable | Palatable | Palatable |

Example 6

A representative oral eliglustat transmucosal delivery system according to the present invention is shown in Table 12 below. Excipients comprising at least one hydrophilic viscosity modifying agent were mixed with eliglustat, and the mixture was compressed into tablets or lollipops. One unit dose of the eliglustat formulation was dispersed in deionized water having a quantity of three times the weight of the eliglustat formulation and the viscosity as measured at various shear rates is presented in Table 13.

TABLE 12

| Component | mg/dose |
|---|---|
| Eliglustat Tartrate (equivalent to 8.4 mg of eliglustat) | 10 |
| Mannitol | 78 |
| Sorbitol | 100 |
| HPMC K4M | 50 |
| Xanthan gum | 6 |
| Sodium Dihydrogen Phosphate | 48.425 |
| Sucralose | 0.5 |
| Peppermint Flavor | 0.5 |
| Menthol | 0.5 |
| Neohesperidine Dihydrochalcone | 0.075 |
| Magnesium Stearate | 3 |
| Talc | 3 |
| TOTAL | 300 |

TABLE 13

| Shear rates (/sec) | Viscosity (Poise) |
|---|---|
| 1 | 463.2 |
| 10 | 55.76 |
| 100 | 7.33 |

Example 7

A representative oral eliglustat transmucosal delivery system according to the present invention is shown in Table 14 below. Excipients comprising at least one hydrophilic viscosity modifying agent were mixed with eliglustat, and the mixture was compressed into tablets or lollipops. One unit dose of the eliglustat formulation was dispersed in deionized water having a quantity of three times the weight of the eliglustat formulation and the viscosity as measured at various shear rates is presented in Table 15.

TABLE 14

| Component | mg/dose |
|---|---|
| Eliglustat Tartrate (equivalent to 8.4 mg of eliglustat) | 10 |
| Mannitol | 78 |
| Sorbitol | 100 |
| Hypromellose K4M | 50 |
| Polycarbophil | 6 |
| Sodium Dihydrogen Phosphate | 48.425 |
| Sucralose | 0.5 |
| Peppermint Flavor | 0.5 |
| Menthol | 0.5 |
| Neohesperidine Dihydrochalcone | 0.075 |
| Magnesium Stearate | 3 |
| Talc | 3 |
| TOTAL | 300 |

TABLE 15

| Shear rates (/sec) | Viscosity (Poise) |
|---|---|
| 1 | 271.5 |
| 10 | 44.78 |
| 100 | 4.05 |

Example 8

A representative oral eliglustat transmucosal delivery system according to the present invention is shown in Table 16 below. Excipients comprising at least one hydrophilic viscosity modifying agent were mixed with eliglustat, and the mixture was compressed into tablets or lollipops. One unit dose of the eliglustat formulation was dispersed in deionized water having a quantity of three times the weight of the eliglustat formulation and the viscosity as measured at various shear rates is presented in Table 17.

TABLE 16

| Component | mg/dose |
|---|---|
| Eliglustat Tartrate (equivalent to 8.4 mg of eliglustat) | 10 |
| Isomalt | 78 |
| Sorbitol | 100 |
| Hypromellose K4M | 50 |
| Polyox 303 | 6 |
| Sodium Dihydrogen Phosphate | 48.425 |
| Sucralose | 0.5 |
| Peppermint Flavor | 0.5 |
| Menthol | 0.5 |
| Neohesperidine Dihydrochalcone | 0.075 |
| Magnesium Stearate | 3 |
| Talc | 3 |
| TOTAL | 300 |

TABLE 17

| Shear rates (/sec) | Viscosity (Poise) |
|---|---|
| 1 | 111.3 |
| 10 | 22.21 |
| 100 | 0.92 |

Example 9

A representative oral eliglustat transmucosal delivery system according to the present invention is shown in Table 18 below. Excipients comprising at least one hydrophilic viscosity modifying agent were mixed with eliglustat, and the mixture was compressed into tablets or lollipops. The compacted mass was moist heated at about 60° C. to form a pliable mass. One unit dose of the eliglustat formulation was dispersed in deionized water having a quantity of three times the weight of the eliglustat formulation and the viscosity as measured at various shear rates is presented in Table 19.

TABLE 18

| Component | mg/dose |
|---|---|
| Eliglustat Tartrate (equivalent to 8.4 mg of eliglustat) | 10 |
| Sorbitol Powder | 70 |
| Gelatin (Type A) | 125 |
| Xanthan Gum | 20 |
| Lecithin Soya NF/EP Powder | 20 |
| Di-Sodium Hydrogen Phosphate | 5 |
| TOTAL | 250 |

TABLE 19

| Shear rates (/sec) | Viscosity (Poise) |
|---|---|
| 1 | 5565 |
| 10 | 561.9 |
| 100 | 46.78 |

Example 10

A representative oral eliglustat transmucosal delivery system according to the present invention is shown in Table 20 below. Eliglustat was solubilized and/or dispersed in excipients comprising at least one hydrophilic viscosity modifying agent and the mixture was casted into films. The films have a square shape having a thickness of about 1 mm and a length of about 20 mm. One unit dose of the eliglustat formulation was dispersed in deionized water having a quantity of three times the weight of the eliglustat formulation and the viscosity as measured at various shear rates is presented in in Table 21.

TABLE 20

| Component | mg/dose |
|---|---|
| Eliglustat Tartrate (equivalent to 8.4 mg of eliglustat) | 20 |
| Modified Starch | 188 |
| Sorbitol | 100 |
| Xanthan gum | 40 |
| Hypromellose K4M | 20 |

TABLE 20-continued

| Component | mg/dose |
|---|---|
| Sucralose | 10 |
| Soy Lecithin | 12 |
| Peppermint Flavor | 4 |
| Menthol | 4 |
| Neohesperidine Dihydrochalcone | 2 |
| Purified Water* | — |
| TOTAL | 400 |

*Removed during the manufacturing process.

TABLE 21

| Shear rates (/sec) | Viscosity (Poise) |
|---|---|
| 1 | 2223 |
| 10 | 269.6 |
| 100 | 36.39 |

Example 11

A representative oral eliglustat transmucosal delivery system according to the present invention is shown in Table 22 below. Eliglustat was solubilized and/or dispersed in excipients comprising at least one hydrophilic viscosity modifying agent and the mixture was casted into films. The mold was tailored to cast single dose films having a square or rectangular shape with a thickness of not less than 1 mm and the longest dimension of not more than 30 mm. One unit dose of the eliglustat formulation was dispersed in deionized water having a quantity of three times the weight of the eliglustat formulation and the viscosity as measured at various shear rates is presented in Table 23.

TABLE 22

| Component | mg/dose |
|---|---|
| Eliglustat Tartrate (equivalent to 8.4 mg of eliglustat) | 10 |
| Modified Starch | 115 |
| Sorbitol | 70 |
| Mannitol | 25 |
| Hypromellose K4M | 50 |
| Sucralose | 5 |
| Gelatin (Type A) | 20 |
| Peppermint Flavor | 2 |
| Menthol | 2 |
| Neohesperidine Dihydrochalcone | 1 |
| Purified Water* | — |
| TOTAL | 300 |

*Removed during the manufacturing process.

TABLE 23

| Shear rates (/sec) | Viscosity (Poise) |
|---|---|
| 1 | 214.5 |
| 10 | 62.37 |
| 100 | 5.71 |

Example 12

A representative oral eliglustat transmucosal delivery system according to the present invention is shown in Table 24 below. Eliglustat was solubilized and/or dispersed in excipients comprising at least one hydrophilic viscosity modifying agent and the mixture was casted into films. The mold was tailored to cast single dose films having a square or rectangular shape with a thickness of not less than 1 mm and the longest dimension of not more than 30 mm. One unit dose of the eliglustat formulation was dispersed in deionized water having a quantity of three times the weight of the eliglustat formulation and the viscosity as measured at various shear rates is presented in Table 25.

TABLE 24

| Component | mg/dose |
| --- | --- |
| Eliglustat Tartrate (equivalent to 8.4 mg of eliglustat) | 10 |
| Modified Starch | 239 |
| Sorbitol | 120 |
| Xanthan Gum | 4 |
| Sucralose | 10 |
| Soy Lecithin | 12 |
| Peppermint Flavor | 2 |
| Menthol | 2 |
| Neohesperidine Dihydrochalcone | 1 |
| Gelatin (Type A) | 80 |
| Purified Water* | — |
| TOTAL | 480 |

*Removed during the manufacturing process.

TABLE 25

| Shear rates (/sec) | Viscosity (Poise) |
| --- | --- |
| 1 | 983.7 |
| 10 | 85.71 |
| 100 | 14.45 |

Example 13

The formulation prepared according to Table 26 did not exhibit thixotropic property with viscosities of less than 50 poises at 1/sec shear rate and less than 10 poises at 10/sec shear rate, measured by dispersing a unit dose of eliglustat formulation in deionized water having a quantity of not more than three times the weight of the eliglustat formulation (Table 27). The film dosage form upon administration, disseminated in less than 5 minutes in oral cavity thereby incapable of providing an oral cavity residence time of more than about 5 minutes and is considered as an ineffective formulation within the scope of the current invention.

TABLE 26

| Component | mg/dose |
| --- | --- |
| Eliglustat tartrate (equivalent to 8.4 mg of eliglustat) | 10.00 |
| Modified Starch (Lycoat RS 720) | 239.0 |
| Sorbitol (Neosorb P60W) | 120.0 |
| Xanthan Gum | 4.000 |
| Sucralose | 10.00 |
| Soy Lecithin | 12.00 |
| Peppermint Flavor | 2.000 |
| Menthol | 2.000 |
| Neohesperidine Dihydrochalcone (NHDC) | 1.000 |
| Purified Water* | — |
| TOTAL | 400 |

*Removed during the manufacturing process.

TABLE 27

| Shear rates (/sec) | Viscosity (Poise) |
| --- | --- |
| 1 | 2.36 |
| 10 | 1.53 |
| 100 | 1.31 |
| Buccal Residence | ~2 minutes |

Example 14

The formulation prepared according to Table 28 did not exhibit thixotropic property with viscosities of less than 50 poises at 1/sec shear rate and less than 10 poises at 10/sec shear rate, measured by dispersing a unit dose of eliglustat formulation in deionized water having a quantity of not more than three times the weight of the eliglustat formulation (Table 29). The film dosage form upon administration, disseminated in less than 5 minutes in oral cavity thereby incapable of providing an oral cavity residence time of more than about 5 minutes and is considered as an ineffective formulation within the scope of the current invention.

TABLE 28

| Component | mg/dose |
| --- | --- |
| Eliglustat tartrate (equivalent to 8.4 mg of eliglustat) | 10.00 |
| Modified Starch (Lycoat RS 720) | 145.0 |
| Sorbitol (Neosorb P60W) | 30.0 |
| Tween 80 | 1.000 |
| Sucralose | 4.00 |
| Soy Lecithin | 5.00 |
| Peppermint Flavor | 2.000 |
| Menthol | 2.000 |
| Neohesperidine Dihydrochalcone (NHDC) | 1.000 |
| Purified Water* | — |
| TOTAL | 200 |

*Removed during the manufacturing process.

TABLE 29

| Shear rates (/sec) | Viscosity (Poise) |
| --- | --- |
| 1 | 1.86 |
| 10 | 1.61 |
| 100 | 1.54 |
| Buccal residence | ~2 minutes |

What is claimed is:

1. An oral transmucosal dosage form comprising a non-disintegrating solid mass comprising:
    a. a hydrophilic viscosity modifying agent selected from a natural or a synthetic gum with a molecular weight of 10,000 Daltons or greater,
    b. a buffering agent, and
    c. not more than 70 mg eliglustat,
    wherein the dosage form is 500 mg or less and provides an oral cavity residence time of at least about 5 minutes, and wherein the dosage form generates a microenvironment inside the oral cavity exhibiting a thixotropic behavior with viscosities of at least 50 poises at 1/sec shear rate and at least 10 poises at 10/sec shear rate.

2. The oral transmucosal delivery system of claim 1, wherein the eliglustat is 5 mg to 20 mg.

3. The oral transmucosal dosage form of claim 1, wherein the eliglustat is eliglustat is eliglustat tartrate or eliglustat hemitartrate.

4. The oral transmucosal dosage form of claim 1, wherein the buffering agent is a phosphate buffer, citrate buffer, organic buffer, mineral buffer, or combinations thereof.

5. The oral transmucosal dosage form of claim 1, wherein the buffering agent is disodium hydrogen phosphate.

6. The oral transmucosal dosage form of claim 1, wherein the hydrophilic viscosity modifying agent is selected from:
   a. a natural gum selected from the group consisting of acacia, tragacanth, xanthan gum, alginates, agar, carrageenan, karaya gum, guar gum, locust bean gum, modified starch, gelatin and combinations thereof;
   b. synthetic gum selected from the group consisting of a carbomer, polycarbophil, povidone (polyvinylpyrrolidone), polydextrose, polyethylene oxide (PEO), cellulose derivative, and combinations thereof; or
   c. combinations thereof.

7. The oral transmucosal dosage form of claim 6, wherein the cellulose derivative is selected from the group consisting of hydroxypropyl methyl cellulose, methylcellulose, hydroxypropyl cellulose, hydroxyethyl cellulose, carboxymethylcellulose sodium, and combinations thereof.

8. The oral transmucosal dosage form of claim 1, comprising at least two hydrophilic viscosity modifying agents.

9. The oral transmucosal dosage form of claim 1, further comprising a low molecular weight water soluble component with a molecular weight of less than 10,000 Daltons.

10. The oral transmucosal dosage form of claim 9, wherein at least about 50% (wt/wt) of the non-disintegrating solid mass consists of the hydrophilic viscosity modifying agent, buffering agent and the low molecular weight water soluble component.

11. The oral transmucosal dosage form of claim 9, wherein the low molecular weight water soluble component is selected from the group consisting of monosaccharides, disaccharides, polyols, and combinations thereof.

12. The oral transmucosal dosage form of claim 11, wherein the polyol is selected from the group consisting of sorbitol, mannitol, maltitol, erythritol, hydrogenated starch hydrolysates, xylitol, isomalt, lactitol, and combinations thereof.

13. The oral transmucosal dosage form of claim 1, wherein the dosage form is about 200 mg to about 300 mg.

14. The oral transmucosal dosage form of claim 1, wherein the oral transmucosal dosage form provides an oral cavity residence time of about 10 minutes to about 20 minutes.

15. The oral transmucosal dosage form of claim 1, wherein more than 50% of eliglustat is released from the dosage form within 20 minutes in simulated saliva fluid.

16. The oral transmucosal dosage form of claim 1, wherein the dosage form is a tablet, a lollipop, or a film.

17. A method of making an oral transmucosal dosage form comprising:
   a. mixing (i) a hydrophilic viscosity modifying agent selected from a natural or a synthetic gum with a molecular weight of 10,000 Daltons or greater, (ii) a low molecular weight water soluble component with a molecular weight of less than 10,000 Daltons, (iii) a buffering agent and (iv) eliglustat to form a mixture; and
   b. compacting the mixture into a tablet or a lollipop;
   wherein the dosage form generates a microenvironment inside the oral cavity exhibiting a thixotropic behavior with viscosities of at least 50 poises at 1/sec shear rate and at least 10 poises at 10/sec shear rate.

18. The method of claim 17, further comprising moist heating the compacted mixture to form a pliable dosage form.

19. A method of making an oral transmucosal dosage form comprising:
   a. solubilizing and/or dispersing eliglustat in a mixture of (i) a hydrophilic viscosity modifying agent selected from a natural or a synthetic gum with a molecular weight of 10,000 Daltons or greater, (ii) a low molecular weight water soluble component with a molecular weight of less than 10,000 Daltons, and (iii) a buffering agent; and
   b. casting the mixture into films, wherein the dosage form is 500 mg or less and provides an oral cavity residence time of at least about 5 minutes;
   wherein the dosage form generates a microenvironment inside the oral cavity exhibiting a thixotropic behavior with viscosities of at least 50 poises at 1/sec shear rate and at least 10 poises at 10/sec shear rate.

20. A method of treating a subject with Gaucher disease type 1, the method comprising administering the dosage form of claim 1, wherein the dosage form is administered to the subject without pre-determining the subject's CYP2D6 genotype.

* * * * *